(12) United States Patent
Porter et al.

(10) Patent No.: US 8,206,763 B2
(45) Date of Patent: *Jun. 26, 2012

(54) INSECT REPELLENT CONCENTRATE FORMULATION

(75) Inventors: Lori Ann Porter, Key Largo, FL (US); Powell Porter, Key Largo, FL (US); Jess Storey, Key Largo, FL (US)

(73) Assignees: Lori Ann Porter, Florida City, FL (US); Powell Porter, Florida City, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/114,179

(22) Filed: May 24, 2011

(65) Prior Publication Data

US 2012/0003334 A1    Jan. 5, 2012

Related U.S. Application Data

(63) Continuation of application No. 12/313,077, filed on Nov. 17, 2008, now Pat. No. 7,947,311, which is a continuation-in-part of application No. 11/891,658, filed on Aug. 10, 2007, now abandoned.

(51) Int. Cl.
*A61K 36/00* (2006.01)
*A61K 36/8962* (2006.01)
*A61K 36/534* (2006.01)
*A61K 36/48* (2006.01)

(52) U.S. Cl. ........ 424/739; 424/725; 424/754; 424/747; 424/757

(58) Field of Classification Search .................. None
See application file for complete search history.

*Primary Examiner* — Qiuwen Mi

(74) *Attorney, Agent, or Firm* — Malloy & Malloy, P.L.

(57) ABSTRACT

A non-toxic insect repellent concentrate formulation utilizing a plurality of all natural active components has been proven to be effective in repelling mosquitoes for periods of between six to eight weeks, with one application. The insect repellent concentrate formulation includes a plurality of natural essential oils comprising at least one emulsifying agent to maintain the oils in a stable solution. A pH conditioning agent may be added to assure the formulation is pH balanced for application to grass, plants, and trees, without detriment. The formulation may be provided as either a concentrate, or at dilutions ready for direct application, and may be applied by any of a variety of methods including broadcast spraying, boom applicators, misting systems, aerosol spray devices, etc.

6 Claims, No Drawings

INSECT REPELLENT CONCENTRATE FORMULATION

CLAIM OF PRIORITY

The present application is a continuation patent application of previously filed and currently U.S. patent application having Ser. No. 12/313,077 issued as U.S. Pat. No. 7,947,311 and a filing date of Nov. 17, 2008, which is a continuation-in-part patent application having Ser. No. 11/891,658 now abandoned and a filing date of Aug. 10, 2007, each of which are incorporated herein by reference in their entirety.

BACKGROUND

1. Field of the Invention

The present disclosure is directed to a safe, non-toxic, and effective insect repellent concentrate formulation comprising a plurality of active components, including natural essential oils and other natural plant derivatives, which may be diluted in an aqueous carrier solution to obtain an effective concentration which may be safely and liberally applied to a desired area.

2. Description of the Related Art

Mankind has been, literally, plagued by all variety of insects, walking, crawling, swimming, and/or flying since the dawn of time. Mankind has also deployed a variety of means of to eradicate or repel these perceived pests, or both.

In recent history, a number of chemical insecticides have been formulated for agricultural, commercial, and even personal application. A common drawback too many of these formulations is that, while perhaps effective in eradicating or repelling one or more of the intended pests, they also result in the introduction of unnatural toxins into our environment, often with significant side effects. Perhaps the most well know example is the use of dichloro-diphenyl-trichloroethane, or DDT, which was widely used during the second world war to effect widespread elimination of mosquitoes, and subsequently eliminating instances of malaria in vast portions of the world. Unfortunately, it was later discovered that the residual DDT was also adversely affecting the population of large birds of prey, including the American Eagle, among others. Specifically, it was determined that DDT was causing a thinning of the shells and decrease in healthy hatchlings to sustain the populations, which led to widespread bans on the application of DDT in many concerns of the earth.

A common component in many chemical insecticides in use today is pyrethrin which, while considered to be amongst the safest insecticides, is known to irritate eyes, skin, and respiratory systems in humans. In addition, pyrethrin is known to be particularly harmful to aquatic life.

Amongst the numerous issues associated with such chemical insecticides are the safe storage, transport, and handling of many of these chemicals due to the potential hazards they present. As a result, special licenses are often required for personnel transporting and/or applying such chemicals. In addition, special permits are required to store many of these chemicals, not only by the manufacturer and distributor, but by the home or business owner on whose property small quantities, e.g. 55 gallon drums, of a chemical insecticide is temporarily stored for intermittent application on the property. The license and permitting requirements demonstrate not only the hazardous nature of many of these chemical insecticides, but are indicative of additional costs which occur in utilizing such insecticides as a result of specialized training, certification programs, specialized equipment, and/or regulatory oversight.

All of the foregoing precautions in place for storage, transport, and handling of chemical insecticides do not eliminate the airborne hazard presented upon application, as many of these chemicals are designed to be applied by spray or misting systems. Thus, even with all of the precautions to prevent unwanted release of these chemical insecticides into the environment, many of these chemicals are simply sprayed out into the air and are permitted to land where they may, including neighboring property and, perhaps, on the neighbors themselves.

In view of the foregoing, various non-toxic alternatives to such highly toxic insecticides have been developed to either eradicate or repel nuisance insects, such as mosquitoes. One product which has been utilized is the use of candles scented with citronella which, when burned, are intended to repel mosquitoes. However, the effectiveness of this alternative is believed to be minimal, if in fact, effective at all.

As such, it would be beneficial to provide an insect repellent formulation which is non-toxic to the people, plants, and other animals which may be exposed to areas of application. The use of all natural components, or essentially all natural components would also be helpful, thereby eliminating or at least minimizing the production of potentially harmful by-products in the process. A further benefit may be obtained from an insect repellent formulation that comprises long lasting effects, thereby limiting the need for frequent re-application to treated areas.

SUMMARY

As noted above, the present application is directed to a safe, non-toxic, and effective insect repellent formulation comprising natural essential oils and plant derivatives in solution. The insect repellent formulation comprises a plurality of all natural active components including, but in no manner limited to one or more of cinnamon leaf essential oil, garlic essential oil, lemon eucalyptus essential oil, lemongrass essential oil, peppermint essential oil, citronella Java essential oil, and blue raspberry fragrant oil.

The insect repellent formation of the present application also comprises at least one emulsifying agent which, in at least one embodiment, also comprises one or more all natural components. The emulsifying agent is utilized to maintain the plurality of oil based active components in solution, as the insect repellent formulation disclosed in the present application is intended for application via an aqueous carrier solution, such as, for example, dilution in an amount of water.

In at least one embodiment, an amount of the formulation of the present invention is diluted to a total volume of about 100 gallons which provides an effective dosage for application to about one acre of property, wherein the effective dosage continues to repel insects for a period of about eight and ten weeks. The present formulations have proven effective in repelling mosquitoes, flies, and even rodents, from test application areas.

The insect repellent formulation of the present application also comprises a pH conditioning agent, to further facilitate solubilization and stability of the active components in solution, as well as to assure that the pH of the final aqueous solution is in a range that will not be harmful to plants or animals upon application. In at least one embodiment, the pH conditioning agent also comprises an all natural composition, such as, by way of example, an all natural and non-toxic apple cider vinegar.

At least one embodiment of the present repellent formulation disclosed in the present application comprises a buoyancy agent. In the present application, the buoyancy agent comprises an all natural component which has proven effective in suffocating insect larvae, such as for example, mosquito larvae, in standing bodies of water such as may be present in an area of application. In at least one embodiment, the insect repellent formulation as disclosed in the present application comprises an all natural and non-toxic soybean oil.

DETAILED DESCRIPTION

To begin, the present application is directed to a safe, non-toxic, and effective insect repellent formulation comprising natural essential oil derivatives in solution. In all but one of the embodiments disclosed in the present application, the insect repellent formulation of the present invention further comprises additional components which are also all natural. Further, the present application discloses formulations for a concentrate of the insect repellent formulation, as well as presenting effective dilution rates for various application methods of the insect repellent formulation. At least one embodiment of the present invention comprises an insect repellent formulation in an aqueous carrier solution to facilitate application via various methods including, but not limited to, broadcast spraying techniques, boom spraying techniques, misting systems, just to name a few.

The insect repellent formulation comprises a plurality of active components including, but in no manner limited to one or more of all natural cinnamon leaf essential oil, garlic essential oil, lemon eucalyptus essential oil, lemongrass essential oil, peppermint essential oil, citronella Java essential oil, and blue raspberry fragrant oil. Each of the essential oils and the fragrant oil identified above are readily available from a variety of sources, such as, New Directions Aromatics, Inc., San Ramon, Calif. ("New Directions"). More in particular, examples of essential oils and fragrant oils suitable for utilization in the present invention include cinnamon leaf essential oil—New Directions Product Number 11034, garlic essential oil—New Directions Product Number 11058, lemon eucalyptus essential oil—New Directions Product Number 11082, lemongrass essential oil—New Directions Product Number 11080, peppermint essential oil—New Directions Product Number 11115, citronella Java essential oil—New Directions Product Number 11229, and blue raspberry fragrant oil—New Directions Product Number 23061. Table 1 below provides one example of the amounts of each of the essential oils and fragrant oils in one embodiment, Formulation I, of the insect repellent formulation of the present invention.

TABLE 1

Formulation I

| Component | % Volume | Fluid Oz/100 Gal |
|---|---|---|
| Cinnamon Leaf Essential Oil | 0.1 | 12.8 |
| Garlic Essential Oil | 0.1 | 12.8 |
| Lemon *Eucalyptus* Essential Oil | 0.1 | 12.8 |
| Peppermint Essential Oil | 0.05 | 6.4 |
| *Citronella* Java Essential Oil | 0.1 | 12.8 |
| Blue Raspberry Fragrant Oil | 0.05 | 6.4 |
| Subtotal Active Components: | 0.5 | 64 |
| Emulsifying Agent | 0.0-1.0 | 0-128 |
| pH Conditioning Agent | 1.0-2.0 | 128-256 |
| Subtotal Concentrate: | 1.5-3.5 | 192-448 |
| Carrier Solution (% - Gallons) | 96.5-98.5 | 96.5-98.5 |
| Total - Formulation I: | 100% | 100 Gallons |

As illustrated in Table 1, in addition to the active components, i.e., the essential oils and fragrant oil, the insect repellent formulation of Formulation I comprises a pH conditioning agent, and may include an emulsifying agent. The emulsifying agent is utilized to maintain the plurality of oil based active components in solution. This is a consideration as at least one embodiment of the insect repellent formulation disclosed in the present application is intended for application via an aqueous carrier solution, such as, for example, dilution in an amount of water, for example, to produce 100 gallons of solution of the insect repellent formulation which is ready for direct application. Also as noted above, in at least one embodiment, the emulsifying agent comprises one or more all natural components. In at least one embodiment, the emulsifying agent of Formulation I comprises an all natural castile soap. In one alternate embodiment, the emulsifying agent comprises all natural soybean oil which, as discussed below, may also serve as a buoyancy agent.

Also as shown in Table 1, the insect repellent of Formulation I comprises a pH conditioning agent, to further facilitate solubilization and stability of the active components in solution, as well as to assure that the pH of the final aqueous solution is in a range that will not be harmful to plants or animals upon application. In addition to facilitating solubilization and stability, the pH conditioning agent is effective in reducing, and in some instances, eliminating, mineral deposits as are often encountered in spray equipment. Such deposits are known to clog spray heads, as well as supply lines, which results in uneven application. The pH conditioning agent may also comprise an all natural composition. In at least one embodiment, an all natural and non-toxic apple cider vinegar is utilized as the pH conditioning agent for use in Formulation I.

It is noted that the specific amounts of the various components identified in Table 1 above, as well as the additional tables presented hereinafter, are presented for illustrative purposes and are not intended to limit the insect repellent formulation of the present application to the exact amounts listed in any of the tables. Rather, it is envisioned that deviations of plus or minus about 20-40 percent of the listed quantities for any one or more of the active components or agents in any of the tables presented herein will result in an insect repellent formulation that is within the scope and intent of the present application.

Turning next to Tables 2-A and 2-B, and corresponding Formulations II-A and II-B, it is seen that the composition of the active components is the same as presented in Table 1. In addition, and as above, all natural apple cider vinegar may be utilized as the pH conditioning agent for the formulations presented below in Tables 2-A and 2-B.

However, it may also be seen that Formulations II-A and II-B comprise a different emulsifying agent than identified for Formulation I. Specifically, Formulations II-A and II-B utilize an emulsifying agent comprising a mixture including esters of alkyl polyoxyethylene ethers. In at least one embodiment, this emulsifying agent is provided in combination with coupling agents and other constituents such as, by way of example only, the composition known as E-Z Mix, a compatibility agent for liquid fertilizer and pesticide mixtures, as is available from Loveland Products, Inc., Greeley, Ill.

Review of the following tables also illustrates that the embodiment of Formulation II-B is essential the same as Formulation II-A with the exception that Formulation II-B comprises a buoyancy agent in the amount of between about one-half to one percent by volume of a total dilution ready for direct application. A corresponding adjustment to the amount of carrier solution in Formulation II-B is also required to account for the addition of the buoyancy agent. As noted above, the buoyancy agent has been found to cause the insect repellent formulation to float on the surface of standing bodies of water present in areas of application. More importantly, in doing so, the buoyancy agent has proven effective in suffocating water borne larvae of various insects, such as mosquitoes. As noted above, in at least one embodiment, the buoyancy agent comprises all natural, safe, and non-toxic soybean oil.

TABLE 2-A

Formulation II-A

| Component | % Volume | Fluid Oz/100 Gal |
|---|---|---|
| Cinnamon Leaf Essential Oil | 0.1 | 12.8 |
| Garlic Essential Oil | 0.1 | 12.8 |
| Lemon *Eucalyptus* Essential Oil | 0.1 | 12.8 |
| Peppermint Essential Oil | 0.05 | 6.4 |
| *Citronella* Java Essential Oil | 0.1 | 12.8 |
| Blue Raspberry Fragrant Oil | 0.05 | 6.4 |
| Subtotal Active Components: | 0.5 | 64 |
| E-Z Mix Emulsifying Agent | 0.125-0.250 | 16-32 |
| pH Conditioning Agent | 1.0-2.0 | 128-256 |
| Subtotal Concentrate: | 1.625-2.75 | 208-352 |
| Carrier Solution (% - Gallons) | 97.25-98.375 | 97.25-98.375 |
| Total Formulation II-A: | 100% | 100 Gallons |

TABLE 2-B

Formulation II-B

| Component | % Volume | Fluid Oz/100 Gal |
|---|---|---|
| Cinnamon Leaf Essential Oil | 0.1 | 12.8 |
| Garlic Essential Oil | 0.1 | 12.8 |
| Lemon *Eucalyptus* Essential Oil | 0.1 | 12.8 |
| Peppermint Essential Oil | 0.05 | 6.4 |
| *Citronella* Java Essential Oil | 0.1 | 12.8 |
| Blue Raspberry Fragrant Oil | 0.05 | 6.4 |
| Subtotal Active Components: | 0.5 | 64 |
| E-Z Mix Emulsifying Agent | 0.125-0.250 | 16-32 |
| pH Conditioning Agent | 1.0-2.0 | 128-256 |
| Buoyancy Agent | 0.5-1.0 | 64-128 |
| Subtotal Concentrate: | 2.125-3.75 | 272-480 |
| Carrier Solution (% - Gallons) | 96.25-97.875 | 96.25-97.875 |
| Total Formulation II-B: | 100% | 100 Gallons |

Tables 3-A-1 through 3-B-2 present corresponding Formulations III-A-1 through III-B-2. Once again, it may be seen that the composition of the active components is the same as presented in Table 1, however, the relative amounts of each have been adjusted in Formulations III-A-2 and III-B-2 to account for the reduction in the amount of carrier solution required to produce a final total volume of 40 gallons of diluted insect repellent formulation ready for direct application. Once again, as above, all natural apple cider vinegar may be utilized as the pH conditioning agent for the formulations presented below in Tables 3-A-1 and 3-B-2.

As also shown in Formulations III-A-1 through III-B-2, a plurality of emulsifying agents are utilized, more in particular, a first and second emulsifying agent are specified. Specifically, Formulations III-A-1 through III-B-2 utilize a first emulsifying agent comprising a sorbitan monooleate. In at least one embodiment, the first emulsifying agent is Lumisorb SMO K, available from Lambert Technologies, Gurnee, Ill. In addition, Formulations III-A-1 through III-B-2 utilize a second emulsifying agent comprising an ethoxylated sorbitan monooleate. In at least one embodiment, the second emulsifying agent is Lumisorb PSMO-20 K, also available from Lambert Technologies, Gurnee, Ill. Also, as noted above with regard to Formulations II-A and II-B, the difference between Formulations III-A-1 and III-B-1, and corresponding Formulations III-A-2 and III-B-2, is that the "B" formulations further comprise a buoyancy agent, with corresponding adjustments in carrier solution amounts to accommodate the same. Once again, in at least one embodiment, the buoyancy agent comprises all natural soybean oil.

TABLE 3-A-1

Formulation III-A-1

| Component | % Volume | Fluid Oz/100 Gal |
|---|---|---|
| Cinnamon Leaf Essential Oil | 0.1 | 12.8 |
| Garlic Essential Oil | 0.1 | 12.8 |
| Lemon *Eucalyptus* Essential Oil | 0.1 | 12.8 |
| Peppermint Essential Oil | 0.05 | 6.4 |
| *Citronella* Java Essential Oil | 0.1 | 12.8 |
| Blue Raspberry Fragrant Oil | 0.05 | 6.4 |
| Subtotal Active Components: | 0.5 | 64 |
| First Emulsifying Agent (sorbitan monooleate) | 0.025 | 3.2 |
| Second Emulsifying Agent (ethoxylated sorbitan monooleate) | 0.125 | 16 |
| pH Conditioning Agent | 1.0-2.0 | 128-256 |
| Subtotal Concentrate: | 1.65-2.65 | 211.2-339.2 |
| Carrier Solution (% - Gallons) | 97.35-98.35 | 97.35-98.35 |
| Total Formulation III-A-1: | 100% | 100 Gallons |

TABLE 3-B-1

Formulation III-B-1

| Component | % Volume | Fluid Oz/100 Gal |
|---|---|---|
| Cinnamon Leaf Essential Oil | 0.1 | 12.8 |
| Garlic Essential Oil | 0.1 | 12.8 |
| Lemon *Eucalyptus* Essential Oil | 0.1 | 12.8 |
| Peppermint Essential Oil | 0.05 | 6.4 |
| *Citronella* Java Essential Oil | 0.1 | 12.8 |
| Blue Raspberry Fragrant Oil | 0.05 | 6.4 |
| Subtotal Active Components: | 0.5 | 64 |
| First Emulsifying Agent (sorbitan monooleate) | 0.025 | 3.2 |
| Second Emulsifying Agent (ethoxylated sorbitan monooleate) | 0.125 | 16 |
| pH Conditioning Agent | 1.0-2.0 | 128-256 |
| Buoyancy Agent | 0.5-1.0 | 64-128 |
| Subtotal Concentrate: | 2.15-3.65 | 275.2-467.2 |
| Carrier Solution (% - Gallons) | 96.35-97.85 | 96.35-97.85 |
| Total Formulation III-B-1: | 100% | 100 Gallons |

TABLE 3-A-2

Formulation III-A-2

| Component | % Volume | Fluid Oz/40 Gal |
|---|---|---|
| Cinnamon Leaf Essential Oil | 0.25 | 12.8 |
| Garlic Essential Oil | 0.25 | 12.8 |
| Lemon *Eucalyptus* Essential Oil | 0.25 | 12.8 |
| Peppermint Essential Oil | 0.125 | 6.4 |
| *Citronella* Java Essential Oil | 0.25 | 12.8 |
| Blue Raspberry Fragrant Oil | 0.125 | 6.4 |
| Subtotal Active Components: | 1.25 | 64 |
| First Emulsifying Agent (sorbitan monooleate) | 0.0625 | 3.2 |

TABLE 3-A-2-continued

Formulation III-A-2

| Component | % Volume | Fluid Oz/40 Gal |
|---|---|---|
| Second Emulsifying Agent (ethoxylated sorbitan monooleate) | 0.3125 | 16 |
| pH Conditioning Agent | 2.5-5.0 | 128-256 |
| Subtotal Concentrate: | 4.125-6.625 | 211.2-339.2 |
| Carrier Solution (% - Gallons) | 93.375-95.875 | 37.35-38.35 |
| Total Formulation III-A-2: | 100% | 40 Gallons |

TABLE 3-B-2

Formulation III-B-2

| Component | % Volume | Fluid Oz/40 Gal |
|---|---|---|
| Cinnamon Leaf Essential Oil | 0.25 | 12.8 |
| Garlic Essential Oil | 0.25 | 12.8 |
| Lemon *Eucalyptus* Essential Oil | 0.25 | 12.8 |
| Peppermint Essential Oil | 0.125 | 6.4 |
| Citronella Java Essential Oil | 0.25 | 12.8 |
| Blue Raspberry Fragrant Oil | 0.125 | 6.4 |
| Subtotal Active Components: | 1.25 | 64.0 |
| First Emulsifying Agent (sorbitan monooleate) | 0.0625 | 3.2 |
| Second Emulsifying Agent (ethoxylated sorbitan monooleate) | 0.3125 | 16 |
| pH Conditioning Agent | 2.5-5.0 | 128-256 |
| Buoyancy Agent | 1.25-2.5 | 64-128 |
| Subtotal Concentrate: | 5.375-9.125 | 275.2-467.2 |
| Carrier Solution (% - Gallons) | 90.875-94.625 | 36.35-37.85 |
| Total Formulation III-B-2: | 100% | 40 Gallons |

Next we turn to Tables 4-A and 4-B and Formulations IV-A and IV-B, respectively, which again comprise the same all natural active components as presented in the preceding formulations. Also as above, Formulations IV-A and IV-B, in at least one embodiment, utilize all natural apple cider vinegar as the pH conditioning agent. In addition, as discussed with regard to the preceding formulations, the distinguishing feature as between Formulation IV-A and Formulation IV-B is that is that the "B" formulation further comprises a buoyancy agent, with a corresponding adjustment in carrier solution amounts to accommodate the same. As above, in at least one embodiment, the buoyancy agent comprises all natural soybean oil.

Of particular interest is that Formulations IV-A and IV-B comprise an all natural emulsifying agent, thereby resulting in completely all natural insect repellent formulation. One embodiment of Formulations IV-A and IV-B utilize a film-forming, non-ethoxylated emulsifying agent comprising a complex of polyglycerine fatty acid esters, fatty alcohol and sodium stearoyl lactylate, which forms a gel matrix structure within an emulsion to which an oil phase attaches. In at least one embodiment, Formulations IV-A and IV-B utilize a polyglyceryl-10 pentastearate, behenyl alcohol, and sodium stearoyl lactylate complex, such as, Nikkomulese-41 BPC, produced by Barnet Products Corporation, Englewood Cliffs, N.J., as the all natural emulsifying agent.

TABLE 4-A

Formulation IV-A

| Component | % Volume | Fluid Oz/100 Gal |
|---|---|---|
| Cinnamon Leaf Essential Oil | 0.1 | 12.8 |
| Garlic Essential Oil | 0.1 | 12.8 |
| Lemon *Eucalyptus* Essential Oil | 0.1 | 12.8 |
| Peppermint Essential Oil | 0.05 | 6.4 |
| Citronella Java Essential Oil | 0.1 | 12.8 |
| Blue Raspberry Fragrant Oil | 0.05 | 6.4 |
| Subtotal Active Components: | 0.5 | 64 |
| Emulsifying Agent (Nikkomulese-41 BPC) | 0.8 | 102 |
| Initial Carrier Solution | 8.7 | 1114 |
| Subtotal Concentrate: | 10.0 | 1280 |
| pH Conditioning Agent | 0.25-1.0 | 32-128 |
| Final Carrier Solution (% - Gal) | 89.0-89.75 | 89.0-89.75 |
| Total Formulation IV-A: | 100% | 100 Gallons |

TABLE 4-B

Formulation IV-B

| Component | % Volume | Fluid Oz/100 Gal |
|---|---|---|
| Cinnamon Leaf Essential Oil | 0.1 | 12.8 |
| Garlic Essential Oil | 0.1 | 12.8 |
| Lemon *Eucalyptus* Essential Oil | 0.1 | 12.8 |
| Peppermint Essential Oil | 0.05 | 6.4 |
| Citronella Java Essential Oil | 0.1 | 12.8 |
| Blue Raspberry Fragrant Oil | 0.05 | 6.4 |
| Subtotal Active Components: | 0.5 | 64 |
| Emulsifying Agent (Nikkomulese-41 BPC) | 0.8 | 102 |
| Buoyancy Agent | 0.5-1.0 | 64-128 |
| Initial Carrier Solution | 7.7-8.2 | 984-1050 |
| Subtotal Concentrate: | 10.0 | 1280 |
| pH Conditioning Agent | 0.25-1.0 | 32-128 |
| Final Carrier Solution (% - Gal) | 89.0-89.75 | 89.0-89.75 |
| Total Formulation IV-B: | 100% | 100 Gallons |

Review of Tables 4-A and 4-B further illustrates that the "concentrate" of both Formulation IV-A and Formulation IV-B comprise an initial amount of carrier solution. These tables further illustrate that the "concentrate" for these formulations do not comprise the pH Conditioning Agent. This is due to the all natural emulsifying agent employed in Formulations IV-A and IV-B. Specifically, an initial amount of carrier solution is required in combination with the active components and the all natural emulsifying agent to maintain a stable, thoroughly homogenous concentrate solution. For the same reason, in at least one embodiment, and as illustrated in Tables 4-A and 4-B, the pH conditioning agent is not added to the "concentrate" of Formulations IV-A or IV-B, rather, it is not added until preparation of a working solution, i.e., dilution with the concentrate into a final amount of carrier solution, just prior to application, as is discussed in greater detail below.

A variation of Formulation IV-A is utilized to produce a base "cream" formulation, by eliminating the carrier solution, which is applied directly to a person or an animal to provide an insect repellent barrier for the person or animal. In such an embodiment, the cream base may be supplemented with one or more additives to further enhance desirability of the formulation. As one example, a sunscreen, for example, titanium dioxide and/or zinc oxide, may be incorporated into the cream base to provide the dual purposes of protection from insect and pests, as well as protecting a user from the harmful rays of the sun. In one further embodiment, an amount of pure and all natural Emu oil may be incorporated into the cream base thereby imparting the beneficial effects of Emu oil to the user, while providing protection from insects and other pests. Yet another embodiment may comprise an amount of andiroba oil, which exhibits analgesic, anti-bacterial and anti-inflammatory properties, and may be incorporated in the cream base either alone, or in combination with one or more of the additives noted above.

The present application further provides, by way of example, processing parameters for a number of the formulations presented above. For example, the formulation presented in Table 2-A may be prepared in accordance with the following. To begin, the specified amount of active components including natural essential oils and other natural plant derivatives, in accordance with Formulation II-A, are blended together with an emulsifying agent comprising a mixture including esters of alkyl polyoxyethylene ethers at a rate of about 1 to 2 parts of emulsifying agent per 4 parts of active components, e.g., 16 to 32 fluid ounces of E-Z Mix Emulsifying Agent to 64 fluid ounces of active components, utilizing a paddle blender at low speed, approximately forty (40) revolutions per minute (rpm), for about five (5) minutes. While still mixing at low speed, a pH conditioning agent is slowly added to the initial mixture in an amount of about 2 to 4 times that of the active components, e.g., 128 to 256 fluid ounces of apple cider vinegar. Following the addition of the pH conditioning agent, continue mixing at low speed for about five (5) minutes. At this point, a concentrate for Formulation II-A is obtained. The foregoing process may be carried out at room temperature and ambient pressure in an open or vented mixing chamber.

The "concentrate" produced in accordance with Formulation II-A and the foregoing process is stable and may be stored at room temperature for extended periods until it is ready for application. A final working solution may be obtained by diluting the concentrate in an appropriate volume of a carrier solution. As one example, the carrier solution comprises water, and the dilution rate may be between about 1.5 and 3.0 percent of concentrate by volume in water. More in particular, and as presented in Table 2-A, an amount of between about 208 and 352 fluid ounces of concentrate is diluted in water to prepare a working solution having a final volume of about 100 gallons, which is suitable for application via broadcast spraying and boom spraying applications. At this dilution, the formulation may also be suitable for application via misting and/or aerosol systems, however, other dilutions may be desired for such misting and/or aerosol applications.

The formulation presented in Table 2-B is prepared essentially as above with one additional step. Specifically, after thoroughly mixing the pH conditioning agent into the concentrate for Formulation II-A, an amount of a buoyancy agent in an amount of between about 1 to 2 times that of the active components is added, e.g., 64 to 128 fluid ounces of soybean oil, is thoroughly blended into the concentrate at low speed for an additional five (5) minutes. As with the foregoing formulation, the concentrate comprising the buoyancy agent will also remain stable at room temperatures for extended periods of time until ready for application. Also as above, this concentrate may be diluted in an appropriate volume of a carrier solution, such as, water, to prepare a working solution for application via broadcast spraying, boom spraying, and possibly misting systems.

The process to produce the formulations presented in Tables 3-A-1 through 3-B-2 is slightly modified from that presented above for Formulations II-A and II-B. In particular, each of the formulations presented in Tables 3-A-1 through 3-B-2 comprises two emulsifying agents. An initial step in the process is the addition of a pH conditioning agent to a first emulsifying agent and blending these components together in a paddle blender. In at least one formulation, the first emulsifying agent comprises a sorbitan monooleate, for example, Lumisorb SMO K, and the pH conditioning agent comprises apple cider vinegar. Once the first emulsifying agent and the pH conditioning agent are thoroughly blended together at low speed for about five (5) minutes, the active components are slowly added and blended in at low speed, once again, about 40 rpm, for another five (5) minutes. Next, the second emulsifying agent is added and the entire concentrate is blended together at low speed for an additional period of about 30 minutes. As presented above in Tables 3-A-1 through 3-B-2, the second emulsifying agent comprises an ethoxylated sorbitan monooleate, such as, Lumisorb PSMO-20 K. At this point, a concentrate in accordance with Formulations III-A-1 and III-A-2 is obtained. To obtain a concentrate in accordance with Formulations III-B-1 or III-B-2, a buoyancy agent, for example, soybean oil, is added prior to the addition of the second emulsifying agent, in the amounts identified in the Tables 3-B-1 and 3-B-2, respectively. As above, this process may be carried out at room temperature and pressure.

As with the concentrate for Formulations II-A and II-B, the concentrates for Formulations III-A-1 through III-B-2 are stable and may be stored for extended periods of time at room temperature, until such time as they are readied for application, i.e., dilution into an appropriate volume of carrier solution, in accordance with the amounts provided above in Tables 3-A-1 through 3-B-2. For example, the concentrate can be used at a dilution of between about 1.5 to 4.0 percent in water for broadcast spray applications. In at least one embodiment, a 100 gallon working solution comprising 2.5 percent of concentrate in water provides an effective application dosage for about one (1) acre of undeveloped land.

Higher dilutions of between about 4.0 to 10.0 percent of concentrate in carrier solution may be utilized to produce a lower total volume for application, e.g., 40 gallons, such as may be desired for farm, residential and commercial sites. For example, field applications using boom spraying equipment are often calibrated for 40 gallons of spray volume per acre.

With regard to the formulations presented in Tables 4-A and 4-B, a further modified process requiring elevated temperatures is required. To begin, the active components and an emulsifying agent, in accordance with the amounts listed in Table 4-A or 4-B, are mixed together at a temperature of between about 167 and 176 degrees Fahrenheit (° F.), forming an "oil phase." As noted above, Formulations IV-A and IV-B utilize an emulsifying agent comprising a complex of polyglyceryl-10 pentastearate, behenyl alcohol, and sodium stearoyl lactylate. In at least one embodiment, the emulsifying agent utilized in Formulations IV-A and IV-B comprise the all natural, plant derived emulsifying agent, Nikkomulese BPC-41. An amount of a carrier solution, for example, water, is also heated to the temperature range of about 167 to 176° F. to form an "aqueous phase," is required for homogenization of the "oil phase" with the all natural emulsifying agent, the amount of carrier solution being between about 8 to 10 times that of the "oil phase." While maintaining temperature in the range of 167 to 176° F., the "oil phase" and the "aqueous phase" are thoroughly mixed together for between about 15 and 20 minutes at high speed, e.g., about 3000 rpm, such as may be achieved in a homogenizer. After high speed mixing, the homogenized solution is permitted to cool to room temperature, thereby forming a stable concentrate in accordance with Formulation IV-A which may be stored for extended periods of time prior to application. As with the preceding formulations, a variation comprising a buoyancy agent such as soybean oil, e.g., Formulation IV-B, may be prepared by adding the buoyancy agent, in an amount of about 1 to 2 times that of the total amount of the active components, to the "oil phase" prior to heating and homogenization with the "aqueous phase."

The concentrates prepared in accordance with Formulations IV-A and IV-B, and the foregoing process, do not comprise a pH conditioning agent, as the acidity of the pH conditioning agent may cause the "oil phase" and "aqueous phase" to at least partially separate after even a limited amount storage time. While this "phase" separation is not detrimental to the effectiveness of the formulations, the end user should thoroughly mix the concentrate prior to further dilution into a carrier solution, to assure even distribution of the active components throughout the entire volume of the resultant working solution. To eliminate potential misapplication which may result from such "phase" separation, the pH conditioning agent can be added at the time of dilution of the concentrate into the final volume of carrier solution, thereby eliminating the need for any aggressive mixing prior to application by the end user. In at least one embodiment, the pH conditioning agent is added in an amount of between about 0.25 and 1.0 percent of the final volume of solution, e.g., one-quarter (¼) to one (1) gallon per one hundred (100) gallons of working solution.

As previously stated, Formulations IV-A and IV-B are produced solely from all natural components, and as such, it is particularly well suited for agricultural, residential, and commercial applications, and may be applied utilizing standard, commercially available pest control spraying equipment at an application rate of about 100 gallons of a working solution per acre. Thus, the amount of concentrate of these formulations required per acre is about 10 gallons.

Table 5 below provides one example of the amounts of each the essential oil in an embodiment which is a variation on Formulation I, replacing lemon eucalyptus essential oil with lemongrass essential oil and eliminating blue raspberry fragrant oil.

TABLE 5

| Formulation V | | |
|---|---|---|
| Component | % Volume | Fluid Oz/100 Gal |
| Cinnamon Leaf Essential Oil | 0.1 | 12.8 |
| Garlic Essential Oil | 0.1 | 12.8 |
| Lemongrass Essential Oil | 0.1 | 12.8 |
| Peppermint Essential Oil | 0.05 | 6.4 |
| Citronella Java Essential Oil | 0.1 | 12.8 |
| Subtotal Active Components: | 0.45 | 57.6 |
| Emulsifying Agent | 0.0-1.0 | 0-128 |
| pH Conditioning Agent | 1.0-2.0 | 128-256 |
| Subtotal Concentrate: | 1.45-3.45 | 185.6-441.6 |
| Carrier Solution (% - Gallons) | 96.55-98.55 | 96.55-98.55 |
| Total - Formulation V: | 100% | 100 Gallons |

Similar to the insect repellent formulation of Formulation I, Formulation V comprises a pH conditioning agent, and may include an emulsifying agent. The emulsifying agent is utilized to maintain the plurality of oil based active components in solution. This is a consideration as at least one embodiment of the insect repellent formulation disclosed in the present application is intended for application via an aqueous carrier solution, such as, for example, dilution in an amount of water, for example, to produce 100 gallons of solution of the insect repellent formulation which is ready for direct application. Also as noted above, in at least one embodiment, the emulsifying agent comprises one or more all natural components. In at least one embodiment, the emulsifying agent of Formulation V comprises an all natural castile soap. In one alternate embodiment, the emulsifying agent comprises all natural soybean oil which, as discussed below, may also serve as a buoyancy agent.

Also as shown in Table 5, the insect repellent of Formulation V comprises a pH conditioning agent which, as in Formulation I, further facilitates solubilization and stability of the active components in solution, as well as to assure that the pH of the final aqueous solution is in a range that will not be harmful to plants or animals upon application. In addition to facilitating solubilization and stability, the pH conditioning agent is effective in reducing, and in some instances, eliminating, mineral deposits as are often encountered in spray equipment. Such deposits are known to clog spray heads, as well as supply lines, which results in uneven application. The pH conditioning agent may also comprise an all natural composition. In at least one embodiment, an all natural and non-toxic apple cider vinegar is utilized as the pH conditioning agent for use in Formulation I.

It is noted that the specific amounts of the various components identified in Table 1, as well as the additional tables presented below, are presented for illustrative purposes and are not intended to limit the insect repellent formulation of the present application to the exact amounts listed in any of the tables. Rather, it is envisioned that deviations of plus or minus about 20-40 percent of the listed quantities for any one or more of the active components or agents in any of the tables presented herein will result in an insect repellent formulation within the scope and intent of the present application.

Turning next to Tables 6-A and 6-B, and corresponding Formulations VI-A and VI-B, it is seen that the composition of the active components is the same as presented in Table 5. In addition, and as above, all natural apple cider vinegar may be utilized as the pH conditioning agent for the formulations presented below in Tables 6-A and 6-B.

However, it may also be seen that Formulations VI-A and VI-B comprise a different emulsifying agent than identified for Formulation V. Specifically, Formulations VI-A and VI-B utilize an emulsifying agent comprising a mixture including esters of alkyl polyoxyethylene ethers. In at least one embodiment, this emulsifying agent is provided in combination with coupling agents and other constituents such as, by way of example only, the composition known as E-Z Mix, a compatibility agent for liquid fertilizer and pesticide mixtures, as is available from Loveland Products, Inc., Greeley, Ill.

Review of the following tables also illustrates that the embodiment of Formulation VI-B is essentially the same as Formulation VI-A with the exception that Formulation VI-B comprises a buoyancy agent in the amount of between about one-half to one percent by volume of a total dilution ready for direct application. A corresponding adjustment to the amount of carrier solution in Formulation VI-B is also required to account for the addition of the buoyancy agent. As noted above, the buoyancy agent has been found to cause the insect repellent formulation to float on the surface of standing bodies of water present in areas of application. More importantly, in doing so, the buoyancy agent has proven effective in suffocating water borne larvae of various insects, such as mosquitoes. As noted above, in at least one embodiment, the buoyancy agent comprises all natural, safe, and non-toxic soybean oil.

TABLE 6-A

Formulation VI-A

| Component | % Volume | Fluid Oz/100 Gal |
|---|---|---|
| Cinnamon Leaf Essential Oil | 0.1 | 12.8 |
| Garlic Essential Oil | 0.1 | 12.8 |
| Lemongrass Essential Oil | 0.1 | 12.8 |
| Peppermint Essential Oil | 0.05 | 6.4 |
| Citronella Java Essential Oil | 0.1 | 12.8 |
| Subtotal Active Components: | 0.45 | 57.6 |
| E-Z Mix Emulsifying Agent | 0.125-0.25 | 16-32 |
| pH Conditioning Agent | 1.0-2.0 | 128-256 |
| Subtotal Concentrate: | 1.575-2.70 | 201.6-345.6 |
| Carrier Solution (% - Gallons) | 97.30-98.425 | 97.30-98.425 |
| Total Formulation VI-A: | 100% | 100 Gallons |

TABLE 6-B

Formulation VI-B

| Component | % Volume | Fluid Oz/100 Gal |
|---|---|---|
| Cinnamon Leaf Essential Oil | 0.1 | 12.8 |
| Garlic Essential Oil | 0.1 | 12.8 |
| Lemongrass Essential Oil | 0.1 | 12.8 |
| Peppermint Essential Oil | 0.05 | 6.4 |
| Citronella Java Essential Oil | 0.1 | 12.8 |
| Subtotal Active Components: | 0.45 | 57.6 |
| E-Z Mix Emulsifying Agent | 0.125-0.250 | 16-32 |
| pH Conditioning Agent | 1.0-2.0 | 128-256 |
| Buoyancy Agent | 0.5-1.0 | 64-128 |
| Subtotal Concentrate: | 2.075-3.70 | 265.6-473.6 |
| Carrier Solution (% - Gallons) | 96.30-97.925 | 96.30-97.925 |
| Total Formulation VI-B: | 100% | 100 Gallons |

Tables 7-A-1 through 7-B-2 present corresponding Formulations VII-A-1 through VII-B-2. Once again, it may be seen that the composition of the active components is the same as presented in Table 5, however, the relative amounts of each have been adjusted in Formulations VII-A-2 and VII-B-2 to account for the reduction in the amount of carrier solution required to produce a final total volume of 40 gallons of diluted insect repellent formulation ready for direct application. Once again, as above, all natural apple cider vinegar may be utilized as the pH conditioning agent for the formulations presented below in Tables 7-A-1 and 7-B-2.

As also shown in Formulations VII-A-1 through VII-B-2, a plurality of emulsifying agents are utilized, more in particular, a first and second emulsifying agent are specified. Specifically, Formulations VII-A-1 through VII-B-2 utilize a first emulsifying agent comprising a sorbitan monooleate. In at least one embodiment, the first emulsifying agent is Lumisorb SMO K, available from Lambert Technologies, Gurnee, Ill. In addition, Formulations VII-A-1 through VII-B-2 utilize a second emulsifying agent comprising an ethoxylated sorbitan monooleate. In at least one embodiment, the second emulsifying agent is Lumisorb PSMO-20 K, also available from Lambert Technologies, Gurnee, Ill. Also, as noted above with regard to Formulations VI-A and VI-B, the difference between Formulations VII-A-1 and VII-B-1, and corresponding Formulations VII-A-2 and VII-B-2, is that the "B" formulations further comprise a buoyancy agent, with corresponding adjustments in carrier solution amounts to accommodate the same. Once again, in at least one embodiment, the buoyancy agent comprises all natural soybean oil.

TABLE 7-A-1

Formulation VII-A-1

| Component | % Volume | Fluid Oz/100 Gal |
|---|---|---|
| Cinnamon Leaf Essential Oil | 0.1 | 12.8 |
| Garlic Essential Oil | 0.1 | 12.8 |
| Lemongrass Essential Oil | 0.1 | 12.8 |
| Peppermint Essential Oil | 0.05 | 6.4 |
| Citronella Java Essential Oil | 0.1 | 12.8 |
| Subtotal Active Components: | 0.45 | 57.6 |
| First Emulsifying Agent (sorbitan monooleate) | 0.025 | 3.2 |
| Second Emulsifying Agent (ethoxylated sorbitan monooleate) | 0.125 | 16 |
| pH Conditioning Agent | 1.0-2.0 | 128-256 |
| Subtotal Concentrate: | 1.60-2.60 | 204.8-332.8 |
| Carrier Solution (% - Gallons) | 97.40-98.40 | 97.40-98.40 |
| Total Formulation VII-A-1: | 100% | 100 Gallons |

TABLE 7-B-1

Formulation VII-B-1

| Component | % Volume | Fluid Oz/100 Gal |
|---|---|---|
| Cinnamon Leaf Essential Oil | 0.1 | 12.8 |
| Garlic Essential Oil | 0.1 | 12.8 |
| Lemongrass Essential Oil | 0.1 | 12.8 |
| Peppermint Essential Oil | 0.05 | 6.4 |
| Citronella Java Essential Oil | 0.1 | 12.8 |
| Subtotal Active Components: | 0.45 | 57.6 |
| First Emulsifying Agent (sorbitan monooleate) | 0.025 | 3.2 |
| Second Emulsifying Agent (ethoxylated sorbitan monooleate) | 0.125 | 16 |
| pH Conditioning Agent | 1.0-2.0 | 128-256 |
| Buoyancy Agent | 0.5-1.0 | 64-128 |
| Subtotal Concentrate: | 2.10-3.60 | 268.8-460.8 |
| Carrier Solution (% - Gallons) | 96.40-97.90 | 96.40-97.90 |
| Total Formulation VII-B-1: | 100% | 100 Gallons |

TABLE 7-A-2

Formulation VII-A-2

| Component | % Volume | Fluid Oz/40 Gal |
|---|---|---|
| Cinnamon Leaf Essential Oil | 0.25 | 12.8 |
| Garlic Essential Oil | 0.25 | 12.8 |
| Lemongrass Essential Oil | 0.25 | 12.8 |
| Peppermint Essential Oil | 0.125 | 6.4 |
| Citronella Java Essential Oil | 0.25 | 12.8 |
| Subtotal Active Components: | 1.125 | 57.6 |
| First Emulsifying Agent (sorbitan monooleate) | 0.0625 | 3.2 |
| Second Emulsifying Agent (ethoxylated sorbitan monooleate) | 0.3125 | 16 |
| pH Conditioning Agent | 2.5-5.0 | 128-256 |
| Subtotal Concentrate: | 4.00-6.50 | 204.8-332.8 |
| Carrier Solution (% - Gallons) | 93.50-96.00 | 37.40-38.40 |
| Total Formulation VII-A-2: | 100% | 40 Gallons |

TABLE 7-B-2

Formulation VII-B-2

| Component | % Volume | Fluid Oz/40 Gal |
|---|---|---|
| Cinnamon Leaf Essential Oil | 0.25 | 12.8 |
| Garlic Essential Oil | 0.25 | 12.8 |
| Lemongrass Essential Oil | 0.25 | 12.8 |
| Peppermint Essential Oil | 0.125 | 6.4 |
| Citronella Java Essential Oil | 0.25 | 12.8 |
| Subtotal Active Components: | 1.125 | 57.6 |
| First Emulsifying Agent (sorbitan monooleate) | 0.0625 | 3.2 |
| Second Emulsifying Agent (ethoxylated sorbitan monooleate) | 0.3125 | 16 |
| pH Conditioning Agent | 2.5-5.0 | 128-256 |
| Buoyancy Agent | 1.25-2.5 | 64-128 |
| Subtotal Concentrate: | 5.25-9.00 | 268.8-460.8 |
| Carrier Solution (% - Gallons) | 91.00-94.75 | 36.40-37.90 |
| Total Formulation VII-B-2: | 100% | 40 Gallons |

Next we turn to Tables 8-A and 8-B and Formulations VIII-A and VIII-B, respectively, which again comprise the same all natural active components as presented in the preceding formulations. Also as above, Formulations VIII-A and VIII-B, in at least one embodiment, utilize all natural apple cider vinegar as the pH conditioning agent. In addition, as discussed with regard to the preceding formulations, the distinguishing feature as between Formulation VIII-A and Formulation VIII-B is that is that the "B" formulation further comprises a buoyancy agent, with a corresponding adjustment in carrier solution amounts to accommodate the same. As above, in at least one embodiment, the buoyancy agent comprises all natural soybean oil.

Of particular interest is that Formulations VIII-A and VIII-B comprise an all natural emulsifying agent, thereby resulting in a completely all natural insect repellent formulation. One embodiment of Formulations VIII-A and VIII-B utilizes a film-forming, non-ethoxylated emulsifying agent comprising a complex of polyglycerine fatty acid esters, fatty alcohol and sodium stearoyl lactylate, which forms a gel matrix structure within an emulsion to which an oil phase attaches. In at least one embodiment, Formulations VIII-A and VIII-B utilize a polyglyceryl-10 pentastearate, behenyl alcohol, and sodium stearoyl lactylate complex, such as, Nikkomulese-41 BPC, produced by Barnet Products Corporation, Englewood Cliffs, N.J., as the all natural emulsifying agent.

TABLE 8-A

Formulation VIII-A

| Component | % Volume | Fluid Oz/100 Gal |
|---|---|---|
| Cinnamon Leaf Essential Oil | 0.1 | 12.8 |
| Garlic Essential Oil | 0.1 | 12.8 |
| Lemongrass Essential Oil | 0.1 | 12.8 |
| Peppermint Essential Oil | 0.05 | 6.4 |
| Citronella Java Essential Oil | 0.1 | 12.8 |
| Subtotal Active Components: | 0.45 | 57.6 |
| Emulsifying Agent (Nikkomulese-41 BPC) | 0.8 | 102 |
| Initial Carrier Solution | 8.7 | 1114 |
| Subtotal Concentrate: | 9.95 | 1273.6 |
| pH Conditioning Agent | 0.25-1.0 | 32-128 |
| Final Carrier Solution (% - Gal) | 89.05-89.80 | 89.05-89.80 |
| Total Formulation VIII-A: | 100% | 100 Gallons |

TABLE 8-B

Formulation VIII-B

| Component | % Volume | Fluid Oz/100 Gal |
|---|---|---|
| Cinnamon Leaf Essential Oil | 0.1 | 12.8 |
| Garlic Essential Oil | 0.1 | 12.8 |
| Lemongrass Essential Oil | 0.1 | 12.8 |
| Peppermint Essential Oil | 0.05 | 6.4 |
| Citronella Java Essential Oil | 0.1 | 12.8 |
| Subtotal Active Components: | 0.45 | 57.6 |
| Emulsifying Agent (Nikkomulese-41 BPC) | 0.8 | 102 |
| Buoyancy Agent | 0.5-1.0 | 64-128 |
| Initial Carrier Solution | 7.7-8.2 | 986-1050 |
| Subtotal Concentrate: | 9.45-10.45 | 1209.6-1337.6 |
| pH Conditioning Agent | 0.25-1.0 | 32-128 |
| Final Carrier Solution (% - Gal) | 88.55-90.30 | 88.55-90.30 |
| Total Formulation VIII-B: | 100% | 100 Gallons |

Review of Tables 8-A and 8-B further illustrates that the "concentrate" of each of Formulation VIII-A and Formulation VIII-B comprises an initial amount of carrier solution. These tables further illustrate that the "concentrate" for these formulations do not comprise the pH Conditioning Agent. This is due to the all natural emulsifying agent employed in Formulations VIII-A and VIII-B. Specifically, an initial amount of carrier solution is required in combination with the active components and the all natural emulsifying agent to maintain a stable, thoroughly homogenous concentrate solution. For the same reason, in at least one embodiment, and as illustrated in Tables 8-A and 8-B, the pH conditioning agent is not added to the "concentrate" of Formulations VIII-A or VIII-B, rather, it is not added until preparation of a working solution, i.e., dilution with the concentrate into a final amount of carrier solution, just prior to application, as is discussed in greater detail below.

A variation of Formulation VIII-A is utilized to produce a base "cream" formulation, by eliminating the carrier solution, which is applied directly to a person or an animal to provide an insect repellent barrier for the person or animal. In such an embodiment, the cream base may be supplemented with one or more additives to further enhance desirability of the formulation. As one example, a sunscreen, for example, titanium dioxide and/or zinc oxide, may be incorporated into the cream base to provide the dual purposes of protection from insect and pests, as well as protecting a user from the harmful rays of the sun. In one further embodiment, an amount of pure and all natural Emu oil may be incorporated into the cream base thereby imparting the beneficial effects of Emu oil to the user, while providing protection from insects and other pests. Yet another embodiment may comprise an amount of andiroba oil, which exhibits analgesic, anti-bacterial and anti-inflammatory properties, and may be incorporated in the cream base either alone, or in combination with one or more of the additives noted above.

The present application further provides, by way of example, processing parameters for a number of the formulations presented above. For example, the formulation presented in Table 6-A may be prepared in accordance with the following. To begin, the specified amount of active components including natural essential oils, in accordance with Formulation VI-A, are blended together with an emulsifying agent comprising a mixture including esters of alkyl polyoxyethylene ethers at a rate of about 1 to 2 parts of emulsifying agent per 4 parts of active components, e.g., 16 to 32 fluid ounces of E-Z Mix Emulsifying Agent to 57.6 fluid ounces of active components, utilizing a paddle blender at low speed, approximately forty (40) revolutions per minute (rpm), for about five (5) minutes. While still mixing at low speed, a pH conditioning agent is slowly added to the initial mixture in an amount of about 2 to 4 times that of the active components, e.g., 128 to 256 fluid ounces of apple cider vinegar. Following the addition of the pH conditioning agent, continue mixing at low speed for about five (5) minutes. At this point, a concentrate for Formulation VI-A is obtained. The foregoing process may be carried out at room temperature and ambient pressure in an open or vented mixing chamber.

The "concentrate" produced in accordance with Formulation VI-A and the foregoing process is stable and may be stored at room temperature for extended periods until it is ready for application. A final working solution may be obtained by diluting the concentrate in an appropriate volume of a carrier solution. As one example, the carrier solution comprises water, and the dilution rate may be between about 1.5 and 3.0 percent of concentrate by volume in water. More in particular, and as presented in Table 6-A, an amount of between about 200 and 350 fluid ounces of concentrate is diluted in water to prepare a working solution having a final volume of about 100 gallons, which is suitable for application via broadcast spraying and boom spraying applications. At this dilution, the formulation may also be suitable for application via misting systems, however, other dilutions may be desired for such misting applications.

The formulation presented in Table 6-B is prepared essentially as above with one additional step. Specifically, after thoroughly mixing the pH conditioning agent into the concentrate for Formulation VI-A, an amount of a buoyancy agent in an amount of between about 1 to 2 times that of the active components is added, e.g., 64 to 128 fluid ounces of soybean oil, is thoroughly blended into the concentrate at low speed for an additional five (5) minutes. As with the foregoing formulation, the concentrate comprising the buoyancy agent will also remain stable at room temperatures for extended periods of time until ready for application. Also as above, this concentrate may be diluted in an appropriate volume of a carrier solution, such as, water, to prepare a working solution for application via broadcast spraying, boom spraying, and possibly misting systems.

The process to produce the formulations presented in Tables 7-A-1 through 7-B-2 is slightly modified from that presented above for Formulations VI-A and VI-B. In particular, each of the formulations presented in Tables 7-A-1 through 7-B-2 comprises two emulsifying agents. An initial step in the process is the addition of a pH conditioning agent to a first emulsifying agent and blending these components together in a paddle blender. In at least one formulation, the first emulsifying agent comprises a sorbitan monooleate, for example, Lumisorb SMO K, and the pH conditioning agent comprises apple cider vinegar. Once the first emulsifying agent and the pH conditioning agent are thoroughly blended together at low speed for about five (5) minutes, the active components are slowly added and blended in at low speed, once again, about 40 rpm, for another five (5) minutes. Next, the second emulsifying agent is added and the entire concentrate is blended together at low speed for an additional period of about 30 minutes. As presented above in Tables 7-A-1 through 7-B-2, the second emulsifying agent comprises an ethoxylated sorbitan monooleate, such as, Lumisorb PSMO-20 K. At this point, a concentrate in accordance with Formulations VII-A-1 and VII-A-2 is obtained. To obtain a concentrate in accordance with Formulations VII-B-1 or VII-B-2, a buoyancy agent, for example, soybean oil, is added prior to the addition of the second emulsifying agent, in the amounts identified in the Tables 7-B-1 and 7-B-2, respectively. As above, this process may be carried out at room temperature and pressure.

As with the concentrate for Formulations VI-A and VI-B, the concentrates for Formulations VII-A-1 through VII-B-2 are stable and may be stored for extended periods of time at room temperature, until such time as they are readied for application, i.e., dilution into an appropriate volume of carrier solution, in accordance with the amounts provided above in Tables 7-A-1 through 7-B-2. For example, the concentrate can be used at a dilution of between about 1.5 to 4.0 percent in water for broadcast spray applications. In at least one embodiment, a 100 gallon working solution comprising 2.5 percent of concentrate in water provides an effective application dosage for about one (1) acre of undeveloped land. Higher dilutions of between about 4.0 to 10.0 percent of concentrate in carrier solution may be utilized to produce a lower total volume for application, e.g., 40 gallons, such as may be desired for farm, residential and commercial sites. For example, field applications using boom spraying equipment are often calibrated for 40 gallons of spray volume per acre.

With regard to the formulations presented in Tables 8-A and 8-B, a further modified process requiring elevated temperatures is required. To begin, the active components and an emulsifying agent, in accordance with the amounts listed in Table 8-A or 8-B, are mixed together at a temperature of between about 167 and 176 degrees Fahrenheit (° F.), forming an "oil phase." As noted above, Formulations VIII-A and VIII-B utilize an emulsifying agent comprising a complex of polyglyceryl-10 pentastearate, behenyl alcohol, and sodium stearoyl lactylate. In at least one embodiment, the emulsifying agent utilized in Formulations VIII-A and VIII-B comprise the all natural, plant derived emulsifying agent, Nikkomulese BPC-41. An amount of a carrier solution, for example, water, is also heated to the temperature range of about 167 to 176° F. to form an "aqueous phase," is required for homogenization of the "oil phase" with the all natural emulsifying agent, the amount of carrier solution being between about 8 to 10 times that of the "oil phase." While maintaining temperature in the range of 167 to 176° F., the "oil phase" and the "aqueous phase" are thoroughly mixed together for between about 15 and 20 minutes at high speed, e.g., about 3000 rpm, such as may be achieved in a homogenizer. After high speed mixing, the homogenized solution is permitted to cool to room temperature, thereby forming a stable concentrate in accordance with Formulation VIII-A which may be stored for extended periods of time prior to application. As with the preceding formulations, a variation comprising a buoyancy agent such as soybean oil, e.g., Formulation VIII-B, may be prepared by adding the buoyancy agent, in an amount of about 1 to 2 times that of the total amount of the active components, to the "oil phase" prior to heating and homogenization with the "aqueous phase."

The concentrates prepared in accordance with Formulations VIII-A and VIII-B, and the foregoing process, do not comprise a pH conditioning agent, as the acidity of the pH conditioning agent may cause the "oil phase" and "aqueous phase" to at least partially separate after even a limited amount storage time. While this "phase" separation is not detrimental to the effectiveness of the formulations, the end user should thoroughly mix the concentrate prior to further dilution into a carrier solution, to assure even distribution of the active components throughout the entire volume of the resultant working solution. To eliminate potential misapplication which may result from such "phase" separation, the pH conditioning agent can be added at the time of dilution of the concentrate into the final volume of carrier solution, thereby eliminating the need for any aggressive mixing prior to application by the end user. In at least one embodiment, the pH conditioning agent is added in an amount of between about 0.25 and 1.0 percent of the final volume of solution, e.g., one-quarter (¼) to one (1) gallon per one hundred (100) gallons of working solution.

As previously stated, Formulations VIII-A and VIII-B are produced solely from all natural components, and as such, it is particularly well suited for agricultural, residential, and commercial applications, and may be applied utilizing standard, commercially available pest control spraying equipment at an application rate of about 100 gallons of a working solution per acre. Thus, the amount of concentrate of these formulations required per acre is about 10 gallons.

Table 9 below provides an example of yet another all natural formulation, Formulation IX, which is a concentrate of an insect repellent in accordance with the present invention.

TABLE 9

Formulation IX (Concentrate)

| Component | % Weight |
|---|---|
| Cinnamon Leaf Essential Oil | 3.70 |
| Garlic Essential Oil | 3.80 |
| Lemongrass Essential Oil | 3.80 |
| Peppermint Essential Oil | 3.20 |
| Citronella Java Essential Oil | 3.10 |
| Subtotal Active Components: | 17.60 |
| First Emulsifying Agent | 7.09 |
| Second Emulsifying Agent | 36.56 |
| pH Conditioning Agent | 38.75 |
| Subtotal Non-Active Components: | 82.40 |
| Total Formulation IX (Concentrate) | 100.00% |

Table 9 illustrates that Formulation IX, a concentrated insect repellant formulation which may be diluted in water, or other suitable carrier solution prior to application, comprises all natural active components, namely, cinnamon leaf, garlic, lemongrass, peppermint, and citronella Java essential oils. Further, in at least one embodiment of Formulation IX as shown in Table 9, and in order to provide a completely natural formulation, the first emulsifying agent comprises a lecithin compound such as, by way of example only, ALCOLEC® EM, which is available from the American Lecithin Company of Oxford, Conn.

In addition, and consistent with the goal of providing a completely natural formulation, soybean oil is utilized as the second emulsifying agent in the present formulation. In a number of the foregoing formulations, soybean oil has been included as a buoyancy agent, however, in the development of the concentrate Formulation IX, as presented above in Table 9, it has been determined that the soybean oil is actually dispersed into the solution, and does not float on the surface or otherwise serve as a buoyancy agent. It is believed that the pH conditioning agent serves to "break up" the soybean oil into small miscible droplets, thereby precluding or at least significantly inhibiting its otherwise buoyant characteristics.

Finally, and again in the interest of providing a completely natural formulation, the pH conditioning agent in at least one embodiment of Formulation IX comprises acetic acid, in the form of apple cider vinegar. As noted above, it is believed that the pH conditioning agent interacts with the soybean oil to significantly inhibit the oil's buoyant characteristics.

It will be appreciated from the foregoing that Formulation IX is representative of a concentrate which may be subsequently mixed into an appropriate amount of a carrier solution, such as, by way of example only, water, prior to application. A concentrate formulation prepared in accordance with Table 9 will remain stable and effective for an extended period of time provided it is properly stored in a cool dry place, and at room temperature. Table 10 below presents a few examples of effective mixing rates of the concentrate of Formulation IX in a carrier solution, such as water:

TABLE 10

Dilution Rate for Formulation IX Concentrate

| Volume of Concentrate | Volume of Carrier Solution |
|---|---|
| 3.2 oz | 1 gallon |
| 1.0 pt | 5 gallons |
| 1.0 qt | 10 gallons |
| 2.0 qt | 20 gallons |
| 4.0 qt | 40 gallons |
| 5.0 qt | 50 gallons |
| 10.0 qt | 100 gallons |

When the concentrate of Formulation IX is diluted into water in accordance with the dilution rates presented in Table 10 above, one (1) gallon of concentrate mixed with 40 gallons of water will be effective for treating about 0.4 acres, or approximately 17,500 square feet. Further, a full acre may be treated with a volume of 2.5 gallons, i.e., 10 quarts, of the concentrate of Formulation IX mixed into 100 gallons of water, also in accordance with Table 10. As with the previously defined formulations, upon dilution, the concentrate of Formulation IX may be applied to a treatment area via a pump up sprayer, spray tank, mister or aerosol dispersion device, just to name a few.

Application of the concentrate of Formulation IX, mixed in water in accordance with Table 10, has proven effective in repelling a variety of flying and crawling insects including, but not limited to, mosquitoes, flies, thrips, aphids, millipedes, noseeums, sod webworms, spidermites, whitefly, chinch bugs, armyworms, cutworms, billbugs, ticks, fleas, carpenter ants, and carpenter bees. Formulation IX has also been found to be an effective repellant for other pests or nuisances such as, and again, by way of example only, rats, mice, lizards, deer, and more.

A variation of Formulation IX may also be utilized to produce a base "cream" formulation, by eliminating the carrier solution, which is applied directly to a person or an animal to provide an insect repellent barrier for the person or animal. In such an embodiment, the cream base may be supplemented with one or more additives to further enhance desirability of the formulation. As one example, a sunscreen, for example, titanium dioxide and/or zinc oxide, may be incorporated into the cream base to provide the dual purposes of protection from insect and pests, as well as protecting a user from the harmful rays of the sun. In one further embodiment, an amount of pure and all natural Emu oil may be incorporated into the cream base thereby imparting the beneficial effects of Emu oil to the user, while providing protection from insects and other pests. Yet another embodiment may comprise an amount of andiroba oil, which exhibits analgesic, anti-bacterial and anti-inflammatory properties, and may be incorporated in the cream base either alone, or in combination with one or more of the additives noted above.

Preparation of the Formulation IX concentrate of Table 9, in at least one embodiment, is as follows. An initial step in the process is to charge an appropriately sized mixing vessel with an amount of a pH conditioning agent, e.g., apple cider vinegar, and begin mixing the solution at high speed, approximately 1750 revolutions per minute ("rpm"). While mixing the pH conditioning agent, the first emulsifying agent, e.g., lecithin, in a corresponding amount as specified in accordance with Table 9 is slowly added to the mixing vessel, and the pH conditioning agent and first emulsifying agent are permitted to thoroughly mix together at high speed for approximately thirty (30) minutes. Next, and again while maintaining high speed mixing, an amount of the second emulsifying agent, e.g., soybean oil, is added to the mixing vessel, again in a corresponding amount as specified in accordance with Table 9.

Once the pH conditioning agent, the first emulsifying agent, and the second emulsifying agent have been introduced into the mixing vessel under high speed mixing conditions, the active components are then added to complete the concentrate formulation. In at least one embodiment, the active components are added. More in particular, in at least one embodiment, the first active ingredient added to the mixing vessel is citronella Java essential oil followed, in order, by lemongrass essential oil, cinnamon leaf essential oil, peppermint essential oil, and garlic essential oil. After all of the active components, i.e., the essential oils, have been added to the pH conditioning agent and the emulsifying agents in the mixing vessel, the entire composition is mixed at high speed for at least an additional thirty (30) minutes to assure a substantially homogenous composition throughout the mixing vessel, such that it may be packaged into a plurality of containers for storage and/or distribution for use. In the event packaging into smaller containers is not accomplished within approximately forty-five (45) minutes of completion of mixing in the active components, the composition in the mixing vessel should be remixed prior to packaging.

The process for preparing the concentrate of Formulation IX may be carried out at room temperature and pressure. As previously indicated, although Table 9 lists specific amounts of each component present in Formulation IX, in terms of relative percent by weight of each component in the final formulation, variations in the amount of any component in the range of about 20% to 40% above or below the listed values are expected to result in an insect repellent formulation which falls within the scope and intent of the present invention.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A non-toxic insect repellent formulation concentrate comprising:
   an amount of cinnamon leaf essential oil of about 3.7% by weight,
   an amount of garlic essential oil of about 3.8% by weight,
   an amount of lemongrass essential oil of about 3.8% by weight,
   an amount of peppermint essential oil of about 3.2% by weight,
   an amount of citronella Java essential oil of about 3.1% by weight,
   an amount of lecithin of about 7.1% by weight,
   an amount of soybean oil of about 36.6% by weight, and
   an amount of apple cider vinegar of about 38.7% by weight.

2. The formulation as recited in claim 1 wherein a single application of said non-toxic insect repellent formulation concentrate at an effective dilution rate repels mosquitoes for a period of about eight weeks.

3. The formulation as recited in claim 2 wherein said effective dilution rate is defined as about 10 quarts of said non-toxic insect repellent formulation concentrate diluted in an amount of water to a total volume of 100 gallons.

4. The formulation as recited in claim 3 wherein application of said non-toxic insect repellent formulation concentrate at said effective dilution rate is non-toxic to plants and animals.

5. The formulation as recited in claim 1 wherein said lecithin comprises an enzyme-modified soy lecithin.

6. A non-toxic insect repellent formulation concentrate wherein application of said formulation at an effective dilution rate is non-toxic to plants and animals, said formulation comprising:
   an amount of cinnamon leaf essential oil of about 3.7% by weight,
   an amount of garlic essential oil of about 3.8% by weight,
   an amount of lemongrass essential oil of about 3.8% by weight,
   an amount of peppermint essential oil of about 3.2% by weight,
   an amount of citronella Java essential oil of about 3.1% by weight,
   an amount of enzyme-modified soy lecithin of about 7.1% by weight,
   an amount of soybean oil of about 36.6% by weight, and an amount of apple cider vinegar of about 38.7% by weight.

* * * * *